(12) United States Patent
Khalil et al.

(10) Patent No.: US 7,592,184 B2
(45) Date of Patent: Sep. 22, 2009

(54) AMMONIA DETECTION AND MEASUREMENT DEVICE

(75) Inventors: Gamal E. Khalil, Redmond, WA (US); David L. Putnam, Redmond, WA (US); Todd W. Hubbard, Seattle, WA (US)

(73) Assignee: Photonic BioSystems, Inc., Sammamish, WA (US)

( * ) Notice: Subject to any disclaimer, the term of this patent is extended or adjusted under 35 U.S.C. 154(b) by 55 days.

(21) Appl. No.: 10/157,209

(22) Filed: May 28, 2002

(65) Prior Publication Data

US 2003/0003589 A1 Jan. 2, 2003

Related U.S. Application Data

(63) Continuation of application No. 09/436,921, filed on Nov. 9, 1999, now abandoned.

(51) Int. Cl.
*G01N 33/00* (2006.01)
*G01N 21/27* (2006.01)
*G01N 21/64* (2006.01)

(52) U.S. Cl. .............. 436/113; 422/55; 422/56; 422/57; 422/61; 422/82.05; 422/82.06; 422/82.07; 422/82.08; 422/82.09; 436/100; 436/101; 436/111; 436/112; 436/116; 436/169; 436/172

(58) Field of Classification Search ............ 422/55–57, 422/61, 82.05–82.09; 436/100–101, 111–113, 436/129, 163, 166, 169, 172
See application file for complete search history.

(56) References Cited

U.S. PATENT DOCUMENTS

| | | | |
|---|---|---|---|
| 3,953,566 A | | 4/1976 | Gore |
| 3,998,591 A | * | 12/1976 | Eckfeldt ................. 422/82.11 |
| 4,187,390 A | | 2/1980 | Gore |
| 4,201,548 A | * | 5/1980 | Tamaoku et al. ............. 436/113 |
| 4,513,087 A | * | 4/1985 | Giuliani et al. ............... 436/96 |
| 4,716,074 A | | 12/1987 | Hurley |
| 4,830,010 A | | 5/1989 | Marshall |
| 4,947,861 A | | 8/1990 | Hamilton |
| 5,013,668 A | * | 5/1991 | Fields ........................ 436/168 |
| 5,308,771 A | * | 5/1994 | Zhou et al. .................... 436/39 |
| 5,315,673 A | * | 5/1994 | Stetter et al. ................... 385/12 |
| 5,322,797 A | * | 6/1994 | Mallow et al. .............. 436/106 |
| 5,366,631 A | | 11/1994 | Adiletta |
| 5,415,838 A | * | 5/1995 | Rieger et al. .................. 422/57 |
| 5,494,640 A | * | 2/1996 | Simon et al. ............. 422/82.05 |
| 5,543,621 A | | 8/1996 | Sauke |
| 5,753,285 A | * | 5/1998 | Horan ......................... 426/87 |
| 5,763,360 A | * | 6/1998 | Gundel et al. ............... 502/402 |
| 5,848,975 A | | 12/1998 | Phillips |
| 5,952,237 A | * | 9/1999 | Tanaka et al. ............... 436/101 |
| 6,051,437 A | * | 4/2000 | Luo et al. .................... 436/172 |
| 6,067,989 A | | 5/2000 | Katzman |
| 6,149,952 A | * | 11/2000 | Horan ......................... 426/87 |
| 6,328,932 B1 | * | 12/2001 | Carter et al. ............. 422/82.06 |
| 7,033,839 B1 | * | 4/2006 | Dobler et al. ............... 436/113 |
| 2003/0003589 A1 | | 1/2003 | Khalil |
| 2008/0041136 A1 | | 2/2008 | Kopelman |

FOREIGN PATENT DOCUMENTS

| | | | |
|---|---|---|---|
| EP | 169055 | * | 1/1986 |
| EP | 928966 | * | 7/1999 |
| JP | 57-93253 | * | 6/1982 |
| JP | 61-218941 | * | 9/1986 |
| JP | 3-255943 | * | 11/1991 |
| JP | 5-107240 | * | 4/1993 |
| WO | 98/22813 | * | 2/1998 |

OTHER PUBLICATIONS

KirkBright, G. F. et al, Analyst 1984, 109, 15-17.*
KirkBright, G. F. et al, Analyst 1984, 109, 1025-1028.*
Wyaatt, W. A. et al, Analytical Chemistry 1987, 59, 2272-2276.*
Bacci, M. et al, Analytica Chimica Acta 1988, 207, 343-348.*
Moreno, M. C. et al, Analytica Chimica Acta 1990, 230, 35-40.*
Andres, R. T. et al, Analytica Chimica Acta 1991, 251, 165-168.*
Cui, D. et al, SPIE 1572, 386-391.*
Sellien, W. et al, Analytica Chimica Acta 1992, 269, 83-88.*
Callahan, D. et al, Talanta 1993, 40, 431-444.*
Maher, M. H. et al, Journal of Testing and Evaluation 1993, 21, 448-452.*
Morales-Bahnik, A. et al, Sensors and Actuators, B 1994, 18-19, 493-496.*
Mohr, G. J. et al, Analytica Chimica Acta 1998, 360, 119-128.*
Meredith, D. et al, Water Science Technology 1998, 37, 301-307.*
Sadaoka, Y. et al, Journal of Material Chemistry 1993, 3, 247-251.*
Zhou, Q et al, Applied Optics 1989, 28, 2022-2025.*
Alabbas, S. H. et al, Analytical Proceedings 1989, 26, 373-375.*
Potyrailo, R. A. et al, SPIE 1991, 1572, 434-438.*
Golubkov, S. P. et al, SPIE 1992, 1637, 227-232.*
Potyrailo, R. A., SPIE 1993, 2069, 76-84.*
Klein, R. et al, Fresenius' Journal of Analytical Chemistry 1994, 349, 394-398.*
Potyrailo, R. A. et al, Analyst 1994, 119, 443-448.*
Mills, A. et al, Mikrochimica Acta 1995, 121, 225-236.*
Baron, M. G. et al, Sensors and Actuators, B 1996, 34, 511-515.*
Spear, S. K. et al, Applied Biochemistry and Biotechnology 1998, 75, 175-184.*
Opilski, Z. et al, SPIE 1999, 3731, 172-178.*
Gisclard, J. B. et al, American Industrial Hygiene Association Quarterly 1953, 14, 23-25.*

(Continued)

*Primary Examiner*—Arlen Soderquist
(74) *Attorney, Agent, or Firm*—Barry L. Davison, J.D.; Davis Wright Tremaine LLP

(57) ABSTRACT

There is disclosed an apparatus and method for detecting and measuring volatile acidic or basic components including ammonia, ammonium, or volatile amines (compound) in a gas or liquid state fluid. Specifically, the present invention provides a PTFE-carrier solid phase indicator film having an ammonia-sensitive indicator dye embedded therein, such that the dye moiety changes color or spectral properties upon exposure to the compound to be detected.

23 Claims, No Drawings

OTHER PUBLICATIONS

Bogomolov, M. A. et al, Avtomatizatsiya Khimicheskikh Proizvodstv 1968, 66-73.*
Beswick, R. B. et al, Journal of Colloid and Interface Science 1988, 124, 146-155.*
Kvasnik, F. et al, SPIE 1990, 1172, 75-82.*
Nevzorov, A. A. et al, Khimicheskaya Fizika 1994, 13, 108-115.*
Bondarenko, D. B. et al, Khimicheskaya Fizika 1994, 13, 116-119.*
Novikov, A. F. et al, SPIE 1995, 2550, 119-129.*
Hauser, P. C. et al, Instrumentation Science & Technology 1997, 25, 147-156.*
Malins, C. et al, Sensors and Actuators B 1998, 51, 359-367.*
Fan, S. et al, Huanjing Kexue Xuebao 1999, 19, 200-204.*
Giuliani, J. F. et al, Optics Letters 1983, 8, 54-56.*
Mohr, G. J. et al, Analytical Chemistry 1998, 70, 3868-3873.*
Norena-Franco, L. E. et al, Analyst 1998, 123, 2185-2189.*
Fluoropore Membrane Filter Product Family information, Millipore 1994-2008, 2 pages, http://www.millipore.com/catalogue/item/FHUP04700.*
Millipore Technical Publications "PTFE Membrane Filters" 2001, 2 pages, http://www.millipore.com/techpublications/tech1/pf1044en00.*
Data Sheet "PTFE Membrane Filters" Millipore, 2001, 4 pages, http://www.millipore.com/publications.nsf/a73664f9f981af8c852569b9005b4eee/eb3322447c18c72d85256a6900681859/$FILE/ATTZVFBV/PTFE%20data%20sheet%20PF1044EN00.pdf.*
Graham et al., "Campylobacter Pylori Detected Noninvasively by the 13C-Urea Breath Test," Lancet, May 23, 1987, pp. 1174-1177, vol. 1.
Ito et al., "Hyperammonaemia and *Helicobacter pylori*," Lancet, Jul. 8, 1995, pp. 124-125, vol. 346.
Jicong et al., "15NH4+ Excretion Test: a New Method for Detection of *Helicobacter pylori* Infection," Journal of Clinical Microbiology, Jan. 1992, pp. 181-184, vol. 30.
Lipski et al., "Blood ammonia and *Helicobacter pylori*," Australian & New Zealand Journal of Medicine, Jun. 1992, p. 311, vol. 22.
Marshall et al., "A 20-Minute Breath Test for *Helicobacter pylori*," American Journal of Gastroenterology, Apr. 1991, pp. 438-445, vol. 86.
Mokuolu et al., "Gastric Juice Urease Activity as a Diagnostic Test for *Helicobacter pylori* Infection," American Journal of Gastroenterology, Apr. 1997, pp. 644-648, vol. 92.
Morales-Bahnik et al., "An optochemical ammonia sensor based on immobilized metalloporphyrins," Chemical Abstracts, 1994, vol. 121, abstract 41603j.
NIH Consensus Conference (NIH Consensus Development Panel on *Helicobacter pylori* in Peptic Ulcer Disease), "*Helicobacter pylori* in Peptic Ulcer Disease," JAMA, Jul. 6, 1994, pp. 65-69, vol. 272.
Plevris et al., "Hyperammonaemia in cirrhosis and *Helicobacter pylori* infection," Lancet, Oct. 21, 1995, p. 1104, vol. 346, No. 8982.
Thijs et al., "Diagnostic Tests for *Helicobacter pylori*: A Prospective Evaluation of Their Accuracy, without Selecting a Single Test as the Gold Standard," American Journal of Gastroenterology, Oct. 1996, pp. 2125-2129, vol. 91, No. 10.
Veldhuyzen Van Zanten et al., "14C-Urea Breath Test for the Detection of *Helicobacter pylori*," American Journal of Gastroenterology, Apr. 1990, pp. 399-403, vol. 85, No. 4.

* cited by examiner

AMMONIA DETECTION AND MEASUREMENT DEVICE

RELATED APPLICATION

This application is a continuation application under 37 C.F.R. 1.53(b)(1) of prior application Ser. No. 09/436,921, filed on Nov. 9, 1999 now abandoned, entitled AMMONIA DETECTION AND MEASUREMENT DEVICE, which application is hereby incorporated by reference.

TECHNICAL FIELD OF THE INVENTION

The present invention provides an apparatus and method for detecting and measuring volatile acidic or basic components including ammonia, ammonium, or volatile amines (compound) in a gas or liquid state fluid. Specifically, the present invention provides a PTFE-carrier solid phase indicator film having an ammonia-sensitive indicator dye embedded therein, such that the dye moiety changes color or spectral properties upon exposure to the compound to be detected.

BACKGROUND OF THE INVENTION

Many industries require a means for sensing the presence of volatile acidic or basic chemical compounds in a fluid (gas or liquid). The means should provide a visual indication of the presence of the compound of interest or provide an instrument for monitoring and measuring presence of compounds. Such an apparatus and method is need for a variety of applications, such as identifying toxic gas leaks, and measuring ammonia in water and soil samples.

There are a variety of sensing methods and devices now available, including solution-based reagent chemistry for calorimetric reactions as well as compositions of various solid-phase polymer based (e.g., silicone) optical sensors, which includes paintable indicators for detecting ammonia leaks. In addition to being commonly used for measuring acid and base solutions, pH indicator dyes have been used for sensing ammonia (a basic compound). In some cases the pH indicator dye is contained in a formulation, such as common litmus test paper, or in Drager gas-sampling tubes, that only gaseous ammonia can be measured. Such devices either cannot be exposed to liquids, or can only be exposed to liquids for a brief period, or can only be exposed one time. This problem exists because the indicator dye dissociates from a solid-phase carrier and then leaches into the liquid. In some cases the indicator dye is used in a formulation that is not color reversible. In one case an optical-chemical sensor for ammonium ions was made using porous PTFE (polytetrafluoroethylene) membrane, however, it was only described as applicable to monitoring water, designed for waste-water measurement. It was reported (Sellien et al., *Anal. Chim. Acta,* 269:83-88, 1992) to have the limitation that the indicator was reversible only if the membrane was in contact with an aqueous solution. Therefore, there is a need in the art to improve sensing capabilities for volatile acidic or basic compounds, including and especially ammonia.

SUMMARY OF THE INVENTION

The present invention provides a sensor composition for detecting and measuring volatile acidic or basic compounds in a gas or liquid state fluid, comprising an ammonia-sensitive indicator dye having measurable spectral characteristics immobilized in or on a polytetrafluoroethylene (PTFE) solid substrate, whereby exposure to a volatile acidic or basic compound causes a change in spectral characteristics of the ammonia-sensitive indicator dye. Preferably, the volatile acidic or basic compound is selected from the group consisting of ammonia, ammonium, volatile amines, glacial acetic acid, and combinations thereof. Most preferably, the volatile amines are trimethylamine, dimethylamine, or combinations thereof. Most preferably, the PTFE solid substrate is in the form of a gas-permeable film. Preferably, the ammonia-sensitive indicator dye is selected from the group consisting of bromophenol-blue, bromocreosol green, thymol blue, methyl crystal purple, chlorophenol, free-base porphyrins, Tetraphenylporphyrin ($H_2TPP$), and combinations thereof. Preferably, the solid substrate is particulate PTFE and the sensor composition is suspended in a paste or paint solution for application onto a surface.

The present invention further provides a method for detecting and measuring volatile acidic or basic chemical compounds in a gas or liquid state fluid, comprising:

(a) placing a sensor composition in a environment for detecting volatile acidic or basic chemical compounds, wherein the sensor composition comprises an ammonia-sensitive indicator dye having measurable spectral characteristics, immobilized in or on a solid substrate;

(b) determining the amount of volatile acidic or basic chemical compound present by measuring spectral change in the wavelengths of light (electromagnetic radiation) that are absorbed or emitted by the ammonia-sensitive indicator dye, or by observing a color change.

Preferably, the volatile acidic or basic chemical compound is selected from the group consisting of hydrochloric acid, ammonia, ammonium, volatile amines, glacial acetic acid, and combinations thereof. Preferably, the presence of ammonia, ammonium, or volatile amines present on the sensor composition is determined via a fiberoptic probe placed on the sensor composition. Preferably, the absorbance or luminescent measurement of spectral change is determined with a spectrophotometer.

DETAILED DESCRIPTION OF THE INVENTION

The present invention provides a device and method for detecting and measuring volatile or acidic chemical compounds in a fluid of either a gas or liquid state. In particular, the present invention provides a sensor composition for detecting ammonia, ammonium and/or volatile amines in a gas or liquid state fluid, comprising an ammonia-sensitive indicator dye having measurable spectral characteristics immobilized in or on a solid substrate, whereby exposure to a compound causes a change in spectral characteristics of the dye. Preferably, the solid substrate is PTFE in the form of a film. The PTFE film may be applied on an object or inside a vessel for the purpose of detecting the presence of particular chemical compounds, such as ammonia in the liquid or vapor phase, in the environment to which the film is exposed. A PTFE carrier element is important because PTFE has the adventitious properties of being highly permeable to gases, insoluble in water, and relatively inert to a wide variety of chemical agents. These properties enable the ammonia-sensitive indicator dye to be carried in an insoluble form on a solid-phase construct that reacts quickly when exposed to the chemical compound to which it is sensitive. In addition, it offers protection of the ammonia-sensitive indicator dye in terms of keeping it insolubilized within the PTFE carrier. This can prevent leaching of the ammonia-sensitive indicator dye out of the solid phase in the presence of water or aqueous based liquids. The insoluble form of the ammonia-sensitive indicator dye further prevents reactions with anions and cations, because anions and cations cannot penetrate the PTFE solid phase. The sensor composition is insensitive to nonvolatile chemical species in acidic or basic fluid or aqueous mediums.

The sensor composition is made from an ammonia sensitive indicator dye and a solid phase, preferably a PTFE solid phase in a film form. The sensor compositions are constructed by administering ammonia-sensitive indicator dye(s) in a non-aqueous solvent to a solid-phase PTFE substrate such that the dye is deposited on the solid phase in a form insoluble to aqueous-based solvents. Further, the characteristics of a PTFE film or a porous membrane form are such that it is permeable to gaseous ammonia.

A preferred family of ammonia-sensitive indicator dyes are chromophores (meaning dyes that change color), for example, bromophenol-blue, bromocreosol green dye, thymol blue, methyl crystal purple, and chlorophenol red. Additional ammonia-sensitive indicator dyes include free-base porphyrins, such as $H_2TPP$. These dyes in the sensor composition participate in reversible equilibrium reactions with gaseous ammonia and amine compounds and result in spectral changes in the dye's absorption bands. The acid dissociation constant (pKa) of the ammonia-sensitive indicator dyes determines the relative sensitivity of the sensor composition. For example, the ammonia-sensitive indicator dye bromophenol-blue (pKa=3) has greater sensitivity to gaseous ammonia than bromocresol green (pKa=3.8) and the later has greater sensitivity than phenol red (pKa=7.0). The other major factor that determines the relative sensitivity of the sensing method is the extinction coefficient of the ammonia-sensitive indicator dye. To meet needs for sensing different concentration ranges of ammonia, the type of ammonia-sensitive indicator dye chosen and amount used are thus variable, the selection based mainly on the pKa and extinction coefficient. Other ammonia-sensitive indicator dyes exist that are applicable to the sensing method having dissociation constants (pKa) in the range of about 1 to about 9, water insolubility, solubility in non-aqueous solvents, relative photostability (oxidation potential), and are reasonably "safe" (in terms of a lack of human or animal toxicity). In this regard, preferred luminescent dyes that have shown good sensitivity to ammonia and volatile amine are a class of compounds called free-base porphyrins. These compounds, when they are made to exist in the cation or di-cation forms, react with ammonia or amines producing distinct spectral changes that can be measured either by absorption changes or by fluorescence intensity changes. Free base porphyrins also have different pKa values and hence their sensitivity to ammonia or amine vary depending on the porphyrin ring structure and substitutions.

Ammonia-sensitive indicator dyes are dissolved in an appropriate (non-aqueous) solvent that will wet, penetrate, or dissolve the PTFE substrate. Preferred solvents include, but are not limited to tetrahydrofuran, ethanol, and methanol. The solvent serves as a "carrier" of the ammonia-sensitive indicator dye (or combinations thereof) for application to PTFE solid phase substrates. Exemplary preparations of dye solutions for preparing indicator films for applications involving visual detection are: (a) bromocresol green (Aldrich #11,435-9), 100 mg dissolved in 20 ml methanol; (b) chlorophenol red (Aldrich #19,952-4), 100 mg dissolved in 20 ml methanol; and (c) phenol red (Aldrich #11,452-9), 100 mg dissolved in 20 ml methanol.

Generally, solutions for preparing an ammonia-sensitive indicator dye for application to a PTFE film that will be used for optical measurements are made by dissolving 20 mg of the corresponding dye in 20 ml methanol. Other suitable solution preparations that have been made include chlorophenol red (Aldrich #19,952-4), 22 mg dissolved in 10 ml tetrahydrofuran, bromophenol blue (Aldrich #11,439-1), 10 mg dissolved in 10 ml Ethanol, and bromocresol green (Aldrich #11,435-9), 20 mg dissolved in 10 ml tetrahydrofuran.

PTFE (Teflon®) is the preferred solid phase substrate. The hydrophobicity of the PTFE provides a strong non-covalent bond to bond the dyes. Ammonia diffuses through PTFE easily, making it unnecessary to specify pore sizes or special grades of the PTFE commercial substrate. PTFE material can be easily fabricated and cut into appropriate shapes or configurations for particular sensing applications.

PTFE tapes and film materials from several different manufacturing sources have been used to fabricate inventive ammonia sensor compositions. Use of preformed solid-phase films, membranes, or tapes affords simple and economical manners of fabricating of ammonia sensor compositions. A porous PTFE form is preferred, in order to promote the faster penetration of the gaseous compound into the polymer and reaction with the ammonia sensitive indicator dye immobilized therein. Exemplary PTFE material manufactures whose products have been used as PTFE substrates for sensor compositions in the form of a film include, for example, PTFE thread seal tapes from Plastomer Products Division (Newtown, Pa.), or Furon (Hoosick Falls, N.Y.), and porous PTFE films from Gore-Tex (Elkton, Md.).

A preferred method of fabrication is to dip the PTFE, for instance 2 cm to 5 cm wide PTFE pipe-thread sealing tape strips, into a bath of an indicator dye stock solution. An "indicator stock solution" is an ammonia sensitive indicator dye (or combinations thereof) dissolved in a non-aqueous solvent. This allows ammonia sensitive indicator dye to adhere to the solid phase PTFE to form a "wet" sensor composition. The wet sensor composition is dried at room temperature, or aided with forced air or a drier to facilitate solvent evaporation. The sensor composition (now dried) is then immersed in a fuming 1N-hydrochloric acid solution for 10 minutes. This is followed by a final rinse by immersion in water for 2 minutes. The sensor composition is then left to dry.

Another method for sensor composition fabrication uses a spray gun configuration. The PTFE film, for example, is a sheet of porous Gortex® film. The sheet of PTFE film having two surfaces but only one of which will be treated, for instance, is placed in a ventilated hood. The ammonia-sensitive indicator dye solution (i.e., "stock solution" as termed above) is then sprayed over one or both sides of the PTFE film surface. The ammonia-sensitive indicator dye solution is then left to dry.

The inventive device is based on reaction of the ammonia-sensitive indicator dye with gaseous ammonia, wherein the acid or protonated form of the ammonia-sensitive indicator dye reacts with ammonia. To assure that the ammonia-sensitive indicator dye is in the acid form, the sensor composition is exposed to a fuming hydrochloric acid solution, as described herein, or volatile acid vapors.

The sensor composition is used in stand-alone form (as a free-standing device) to sense the presence of ammonia or other volatile acidic or basic compounds. For example, it is used as a visual sensor by exposing pieces of sensor composition large enough for viewing in an environment to be monitored for ammonia. Sensor composition using bromocresol green as the ammonia-sensitive indicator dye exhibits a reversible color change from yellow towards blue-green to finally a blue hue when exposed to ammonia of respectively increasing concentration in the range of 0 to 5 ppm or greater. Chlorophenol red as an ammonia sensitive indicator dye will exhibit a reversible color change from orange towards magenta and eventually a purple hue when exposed to ammonia of increasing concentration in the range of 0 to 10 ppm or greater. Sensor composition can be immersed directly into water samples for monitoring ammonia. Exposure to, for instance, a basic solution of sodium hydroxide (NaOH) will not produce a color change in a sensor composition made with a pH indicator dye as the ammonia-sensitive indicator dye.

Optical sensors for spectrophotometric detection using a fiber-optic instrument have been built by applying a sensor composition to a distant end or "tip" of an optical fiber. The optical fiber has one end communicating with a spectrophotometer and the second end or "tip" communicating with the sensor composition. The tip is then covered with a second layer of ammonia permeable film, preferably a PTFE film, and the sensor composition and second PTFE film layers are mechanically fixed on the tip using heat-shrink tubing. This configuration provides physical protection of the sensor composition, isolation from liquid mediums, and an optical path of sufficient length for reflective monitoring of spectral change in the ammonia sensor indicator dye. The sensor composition functions adventitiously in a dry state, in contrast to conventional ammonia sensitive electrodes which require a filling solution or buffering condition to be maintained within the sensor element.

Sensor Detection Limit

Prototype sensor compositions are tested in two possible ways. A buffered solution of ammonium chloride ($NH_4Cl$) is made up at a known pH. From the known pKa and concentration of a $NH_4Cl$ solution, one can predict the ammonia concentration in equilibrium with the solution. The sensor composition is then either dipped into the $NH_4Cl$ buffered solution where it comes into equilibrium with the ammonium, or the sensor composition is exposed to headspace gas over the $NH_4Cl$ buffered solution in an enclosed vessel.

Fiber optic-based detection spectrophotometers were used to test sensor compositions made with five different ammonia-sensitive indicator dyes to determine their limit of detection and response time. The sensor compositions were tested using a two-wavelength optical detector system. The response characteristics are shown in the following table.

| PARAMETER | BPB[1] | BCG[2] | CPR[3] | BCP[4] | PR[5] |
|---|---|---|---|---|---|
| Limit of Detection (ppm) | 0.01 | 0.1 | 0.5 | >1.0 | >10 |
| Response time 90% ↑↓ min | 5, 12 | 1.5, 3 | 1, 2 | 1, 1 | 1, 1 |

[1]bromophenol blue, [2]bromocresol green, [3]chlorophenol red, [4]bromocresol purple, [5]phenol red Interference Testing One promising application for solid-phase ammonia indicators in general and the inventive sensor composition in particular is detecting ammonia gas leaks that might occur inside cold food storage rooms that use ammonia as refrigerant. To provide reliable ammonia detection it is important that the ammonia sensor does not respond to other gases that are known to exist within such rooms. Three sensor compositions (distinguished by the choice of ammonia-sensitive indicator dye) were tested for potential interferences of several relevant gases. Results of the tests are tabulated below.

| Interfering Gases | BCG | CPR | PR |
|---|---|---|---|
| Carbon dioxide 100% | No effect | No effect | No effect |
| Oxygen 0% | No effect | No effect | No effect |
| Humidity 100% | No effect | No effect | No effect |
| Ethylene | No effect | | |
| Gases from Pears | No effect | | |
| Gases from Apples | No effect | | |
| Gases from Banana | No effect | | |

Temperature Effect

Two optical sensors were made to evaluate the effect of temperature on ammonia measurements. BCG=bromocresol green and BPB=bromophenol blue dyes were used to fabricate sensor compositions. Sensor compositions were tested in 0.1 ppm, 1.0 ppm and 5 ppm ammonia made from ammonium chloride in pH 7.6 buffer. The sensor compositions were tested at 6° C., 25° C. and 37 ° C. In general, sensor composition sensitivity decreased as the temperature was lowered. The overall sensitivity decreased by 12 % as the temperature was lowered from 37° C. to 6° C. A non-measurable difference was observed between 37° C. and 25° C. For BCG sensor composition, the slope for 1 ppm ammonia change at 6° C. was equal to 9.56 and at 25° C. the slope was equal to 6.67.

Photodetector Alarm Testing

This series of tests describes various absorption methods were used as the basis to monitor spectral changes. A photoelectric fiber-optic contrast sensing instrument manufactured by SICK Optex (Model WLL-160) was used to make an ammonia detection alarm system. The instrument provides a signal output when it senses a pre-calibrated change in light intensity in the optic light path. Optical sensors were fabricated by mounting sensor compositions made with bromocresol green dye onto the fiber optic configurations supplied by SICK Optex. The sensor compositions utilized dyed PTFE films covered by plain PTFE membranes to provide mechanical reinforcement and increased back reflected signal-light return, as described above. The instrument was calibrated to trigger when exposed to a defined ammonia level. This sensing system was tested continuously for four months by exposing the sensor composition every hour to a three-minute ammonia charge, then cycling back to air. The sensor composition performed consistently over this period without the need to re-calibrate, detecting hourly the ammonia exposure condition.

Another photoelectric sensing instrument from SICK Optex—(Model KT5) provides an analog signal output. The KT5 model was used to also test sensor compositions. Pieces of sensor compositions were fixtured in the light path in front of the KT5 instrument's optical window. To measure detection limits to ammonia gas, bromocresol green and bromophenol blue ammonia-sensitive indicator dyes were used to fabricate sensor compositions. Tests were conducted by exposing the sensor compositions to 0.1 ppm, 1.0 ppm, and 10-ppm ammonia, made from ammonium chloride in pH 7.6 buffer. The sensitivity of sensor compositions made with bromocresol green using the KT5 instrument are tabulated below:

KT5 Analog Reading

|  | Ammonia level | | |
| --- | --- | --- | --- |
|  | 0 ppm | 1.0 ppm | 10.0 ppm |
| Sensor 1 | 2.93 | 1.93 | 1.07 |
| Sensor 2 | 2.86 | 1.96 | 1.09 |
| Sensor 3 | 2.75 | 2.03 | 1.07 |
| Sensor 4 | 2.82 | 2 | 1.05 |
| Sensor 5 | 2.77 | 1.97 | 1.06 |
| Sensor 6 | 2.92 | 1.98 | 1.12 |
| Average | 2.842 | 1.978 | 1.077 |
| St Dev | 0.075 | 0.034 | 0.025 |
| Resolution (2 * stdev) |  | 0.079 | 0.284 |

Sensor compositions made with bromocresol green as the ammonia-sensitive indicator dye produced a 48% change for exposure to 1.0 ppm solution and 14% change for 0.1 ppm solutions. Sensor compositions made with bromocresol green as the ammonia-sensitive indicator dye produced 56% change for 1.0 ppm solution and 28% change for 0.1 ppm solutions. Both sensor compositions have the potential of detecting below 0.1 ppm ammonia. Sensor compositions made with bromocresol green as the ammonia-sensitive indicator dye were measured continuously on a KT5 photodetector system for 30 days to determine stability. The sensor composition was cycled between 0 ppm and 5 ppm twice daily. Measurement error as result of signal drift was less than 0.1 ppm.

Fluorescent Techniques

Fluorescence intensity of an indicator dye, for instance, employing a free base porphyrin, can be used to detect ammonia's presence. This example is based on an equilibrium between luminescent (light emitting) free-base porphyrin molecules, where the equilibrium constant is altered by the presence of ammonia. The equilibrium is an acid-base titration example of free base porphyrins. Free-base porphyrins show distinct spectral changes on the addition of either strong acids or strong bases (Austin and Gouterman, *Bioinorg. Chemistry*, 9:281, 1978; and Gouterman and Khalil, *J. Molecular Spectroscopy* 53:88, 1974). For example, free-base porphyrins commonly have four absorption bands in the visible region. Upon adding a strong acid to a porphyrin solution a rapid color change was observed accompanied by reduction of the absorption bands into only two bands.

An indicator solution was prepared by dissolving 20 mg of a free base porphyrin, Tetraphenylporphyrin ($H_2$TPP), in 10 ml methanol to form a pink colored solution. To the $H_2$TPP solution a few drops of concentrated hydrochloric acid was added. The addition of the acid changed the indicator stock solution to a green color. A two square inch piece of PTFE film (Gore-Tex®, 0.2 μm pore size) was immersed into this solution for 30 seconds. The dyed PTFE film was left to dry, producing a green colored sensor composition.

Two pieces of the dried colored sensor composition were placed on top of two separate vials. One vial contained a buffer solution of ammonia chloride that generated the equivalent of 6 ppm of ammonia gas in the vial. The other vial contained only the buffer solution. The sensor compositions, not in contact with the solution surface, were left for 10 minutes of exposure. The sensor composition exposed to the 6 ppm ammonia gas produce a clearly observable reddish emission upon radiating with a hand held UV blacklight-lamp. The other sensor composition showed no visible emission. It should be noted that the sensor composition exposed to the ammonia gas changed color from green to pink, whereas the other did not.

Product Applications

One potential product format for a sensor composition is an indicator-film tape. A flexible tape format for the sensor composition can be placed over or wrapped around vessels, seams, seals, or joints in plumbing lines, for instance, associated with the transfer or containment of ammonia (e.g., ammonia refrigeration systems) for leak detection. The sensor composition in this preferred embodiment is thin PTFE film of the sealant-tape type, and to be used in the same manner as stretchable pipe-thread tape utilized commonly for sealing plumbing joints. The sensor composition in the form of a tape or film is wrapped around and covering an area of interest to provide an indication of leaks. Ammonia escaping through a leak will penetrate the sensor composition tape or film and provide a visually discernable identification of the leak site based on the ammonia-sensitive indicator dye's spectral change. In similar manner of use, the sensor composition can be used to detect holes and defects in objects or materials when ammonia can be applied to one side of the object, such as inside a fuel tank, and the sensor composition is placed on the opposing side.

Tape, which can be peeled off a role, with or without an adhesive component, for use such as pipe-thread tape for sealing or cover objects, has advantage in that it can be easily dispensed and applied in conformal manner to a site for ammonia detection. It can be readily removed and conveniently replaced, whereas a paintable application can not.

In another embodiment of the inventive sensor composition, a gas-permeable protective layer is added to the sensor composition. For some applications it may be advantageous to separate the sensor composition from direct contact with the environment or a physical entity (e.g., container seam) being monitored. This situation applies, for instance, if the sensor film could engender false spectral change due to spurious reactions with the entity being monitored (e.g., due to chemical contaminates or residues on the entity). In such cases, a gas-permeable membrane can be interposed between the sensor composition and the environment being sensed. This can be accomplished with a secondary layer of gas permeable PTFE not containing ammonia-sensitive indicator dye applied to a surface in direct contact with the monitored environment.

In another embodiment of the inventive sensor composition a gas-impermeable protective layer is added to the sensor composition. For some applications it may be advantageous to provide a non-reactive gas-impermeable barrier on one side of the sensor composition. The sensitivity of the ammonia-sensitive indicator dye to gas permeation is increased by limiting the gas transfer through the sensor composition unidirectionally, using a gas-barrier overlay to the ammonia-sensitive indicator dye. The gas-barrier serves to trap gas, reducing its diffusion and escape, thereby increasing its concentration within the sensor composition, and ultimately enhancing spectral change. This embodiment is particularly useful for detecting and pinpointing sites of very small gas leaks, i.e., situations involving small amounts of ammonia.

This configuration is also useful towards protecting the sensor composition per se from exposure to an environment that is not wanted to be monitored, for instance, as might contain substances or contaminates that could produce unwanted spurious spectral changes in the ammonia-sensitive indicator dye. An example is the use of a sensor composition to detect ammonia leaks on a plumbing system. In order to identify specific leak sites on the plumbing, it is undesirable for the sensor composition to be affected by ammonia leaked into the atmosphere potentially causing spectral change throughout one or more indicators due to exposure to ammonia in the general environment.

The sensor composition described is useful for detecting volatile amines as indicated. A useful exemplary application in this regard is the sensing of trimethylamine and dimethylamine. These volatile compounds are produced as a result of microbial activity associated with spoilage of fish and shellfish. The volatile amines liberated from the meat product react with the sensor composition producing a measurable change in a manner that is indicative of the freshness, or alternatively, the state of deterioration of the food product.

The sensor composition for ammonia can also serve as an indicator for similarly measuring compounds that will engender ammonia and/or volatile amines. It can be adapted to detect or measure other compounds in an environment, indirectly, if the compound is subjected to a chemical reaction that liberates gaseous ammonia or amines. In this context, two examples are the sensing of histamine and urea. Histamine can be catalytically cleaved using the enzyme diamine oxidase, and similarly the enzyme urease will cleave urea, both liberating ammonia. The released volatile ammonia is subsequently detected using the sensor composition having a solid-phase ammonia-sensitive indicator dye. For instance, we have measured optically the liberation of ammonia from histamine in a pH 7.4 buffer solution upon addition of diamine oxidase.

The sensor composition can further be employed as a means of detecting or measuring a volatile acid, such as hydrochloric acid. When the sensor composition is in the basic form, such as identified in previously cited cases using exposure to ammonia, it exhibited the spectral characteristic indicative of that form. For instance, the bromocresol green sensor composition attained a blue coloration as indicated. When in the basic form, if exposed to a fuming acid solution or an acid gas vapor, such as was previously described as a means of assuring that the indicator dye is in the acid form, the indicator composition changes. In the case of the bromocresol green sensor composition attaining a yellow color. As such, the described indicator composition can be adapted to detection of a volatile acid per this example. This same utility is similarly illustrated in the example describing the indicator composition made with free base porphyrin, which exhibited changes from red light fluorescent emissive to non-emissive, or from pink to green, when converted from the basic to the acidic form, and visa versa.

We claim:

1. A reversible-in-gas sensor for detecting and measuring volatile basic compounds in a gaseous environment, comprising:
    a polytetraflouroethylene (PTFE) solid substrate; and
    an ammonia-sensitive indicator dye having measurable spectral characteristics immobilized, using a method comprising a volatile acid vapor-treatment, in or on the polytetraflouroethylene (PTFE) solid substrate, the immobilized ammonia-sensitive indicator dye being capable of undergoing a color change in spectral characteristics when exposed to a gaseous environment comprising a volatile basic compound, and further capable of color reversion in a gaseous environment.

2. The sensor of claim 1, wherein the PTFE solid substrate is in the form of a gas-permeable film.

3. The sensor of claim 1, wherein the ammonia-sensitive indicator dye is selected from the group consisting of bromophenol-blue, bromocreosol green, thymol blue, methyl crystal purple, chlorophenol red, tetraphenylporphyrin (H2TPP), and combinations thereof.

4. The sensor of claim 1, wherein the solid substrate is particulate PTFE and the sensor is suspended in a paste or paint solution for application onto a surface.

5. A method for detecting and measuring volatile basic compounds in a gaseous environment, comprising:
    (a) placing a sensor in a gaseous environment comprising a volatile basic compound, wherein the sensor includes an ammonia-sensitive indicator dye having measurable spectral characteristics immobilized, using a method comprising a volatile acid vapor-treatment, in or on the polytetraflouroethylene (PTFE) solid substrate, the immobilized ammonia-sensitive indicator dye capable of undergoing a color change in spectral characteristics when exposed to the gaseous environment comprising the volatile basic compound, and further capable of color reversion in a gaseous environment; and
    (b) determining an amount of volatile basic chemical compound present by measuring a reversible spectral change in the wavelengths of light that are absorbed or emitted by the ammonia-sensitive indicator dye, or by observing a color change.

6. The method of claim 5, wherein the volatile basic chemical compound is selected from the group consisting of ammonia, ammonium, volatile amines, and combinations thereof.

7. The method of claim 6, wherein the volatile amines are trimethylamine, dimethylamine, or combinations thereof.

8. The method of claim 5, wherein the presence of ammonia, ammonium, or volatile amines present on the sensor composition is determined via a fiberoptic probe placed on the sensor composition.

9. The method of claim 5, wherein the absorbance or luminescent measurement of spectral change is determined with a spectrophotometer.

10. The method of claim 5, wherein the gaseous environment in which the immobilized ammonia-sensitive indicator dye is capable of color reversion comprises a volatile acidic compound, the method further comprising:
    placing a sensor in a gaseous environment comprising a volatile acidic compound thereby inducing at least a partial color reversion of the immobilized ammonia-sensitive indicator dye; and
    determining an amount of volatile acid chemical compound present in the gaseous environment by measuring a reversible spectral change in the wavelengths of light that are absorbed or emitted by the ammonia-sensitive indicator dye, or by observing a color change.

11. A method of making a reversible-in-gas sensor for detecting and measuring volatile basic compounds in a gas, comprising:
    dipping a polytetraflouroethylene (PTFE) solid substrate into a bath of a reversible-in-gas, ammonia-sensitive indicator dye having measurable spectral characteristics;
    allowing the indicator dye to adhere to the surface of the solid substrate to form a wet sensor composition;
    allowing the wet sensor composition to dry;
    immersing the dried sensor composition into the vapor phase of a fuming hydrochloric acid solution;
    immersing the sensor in a water bath; and
    allowing the sensor to dry.

12. A method for detecting and measuring ammonia gas leaks inside cold food storage rooms, comprising:
    (a) placing a sensor in a gaseous environment inside a cold food storage room for detecting ammonia gas leaks, wherein the sensor comprises an ammonia-sensitive indicator dye having measurable spectral characteristics immobilized, using a method comprising a volatile acid vapor-treatment step, in or on a polytetraflouroethylene (PTFE) solid substrate, the immobilized ammonia-sensitive indicator dye being capable of undergoing a color change in spectral characteristics when exposed to a gaseous environment comprising ammonia, and further capable of color reversion in a gaseous environment; and (b) determining the amount of ammonia gas present by measuring a reversible spectral change in the wavelengths of light that are absorbed or emitted by the ammonia-sensitive indicator dye, or by observing a color change.

13. The method of claim 11, further comprising:
a non-aqueous solvent in which the reversible, ammonia-sensitive indicator dye is dissolved.

14. The method of claim 13 wherein, the non-aqueous solvent is selected from the group consisting of tetrahydrofuran, ethanol, and methanol.

15. The method of claim 13, wherein the non-aqueous solvent is methanol.

16. The method of claim 13, wherein the non-aqueous solvent is ethanol.

17. The method of claim 13, wherein the non-aqueous solvent is tetrahydrofuran.

18. The sensor of claim 1, wherein the ammonia-sensitive indicator dye is selected from the group consisting of bromophenol-blue, bromocreosol green, thymol blue, methyl crystal purple, chlorophenol red, and combinations thereof.

19. A reversible-in-gas sensor comprising:
a polytetraflouroethylene (PTFE) solid substrate; and
an ammonia-sensitive indicator dye having measurable spectral characteristics immobilized, using a method comprising a volatile acid vapor-treatment, in or on the polytetraflouroethylene (PTFE) solid substrate, the immobilized ammonia-sensitive indicator dye being capable of:
a color change in spectral characteristics when exposed to a gas comprising a volatile basic compound; and
color reversion in a gaseous environment comprising a volatile acidic compound.

20. The sensor of claim 19, wherein the PTFE solid substrate is in the form of a gas-permeable film.

21. The sensor of claim 19, wherein the ammonia-sensitive indicator dye is selected from the group consisting of bromophenol-blue, bromocreosol green, thymol blue, methyl crystal purple, chlorophenol red, tetraphenylporphyrin ($H_2TPP$), and combinations thereof.

22. The sensor of claim 19, wherein the solid substrate is particulate PTFE and the sensor composition is suspended in a paste or paint solution for application onto a surface.

23. A method for detecting and measuring volatile acidic or basic compounds in a gaseous environment, comprising:
placing a sensor in a gaseous environment, the sensor comprising an ammonia-sensitive indicator dye reversibly configurable in an acid form and a basic form, the dye having measurable spectral characteristics immobilized, using a method comprising one of a volatile acid vapor-treatment and a volatile basic vapor-treatment, in or on the polytetraflouroethylene (PTFE) solid substrate, the volatile acid vapor-treatment configuring the dye in the acid form, the volatile basic vapor-treatment configuring the dye in the basic form,
when in the acid form, exposure to a volatile basic chemical compound in the gaseous environment causing the dye to undergoing a reversible color change in spectral characteristics;
when in the basic form, exposure to a volatile acid chemical compound in the gaseous environment causing the dye to undergoing a reversible color change in spectral characteristics; and
determining an amount of volatile acid or basic chemical compound present in the gaseous environment by measuring a reversible spectral change in the wavelengths of light that are absorbed or emitted by the ammonia-sensitive indicator dye, or by observing a color change.

* * * * *

UNITED STATES PATENT AND TRADEMARK OFFICE
CERTIFICATE OF CORRECTION

PATENT NO. : 7,592,184 B2  Page 1 of 1
APPLICATION NO. : 10/157209
DATED : September 22, 2009
INVENTOR(S) : Khalil et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 421 days.

Signed and Sealed this

Twenty-first Day of September, 2010

David J. Kappos
*Director of the United States Patent and Trademark Office*